(12) United States Patent
Saitoh et al.

(10) Patent No.: US 8,366,675 B2
(45) Date of Patent: Feb. 5, 2013

(54) CATHETER CONNECTOR

(75) Inventors: Hideya Saitoh, Tokyo (JP); Toru Yamazaki, Tokyo (JP)

(73) Assignee: Unisis Corporation, Tokyo (JP)

( * ) Notice: Subject to any disclaimer, the term of this patent is extended or adjusted under 35 U.S.C. 154(b) by 188 days.

(21) Appl. No.: 12/935,348

(22) PCT Filed: Mar. 18, 2009

(86) PCT No.: PCT/JP2009/055229
§ 371 (c)(1),
(2), (4) Date: Sep. 29, 2010

(87) PCT Pub. No.: WO2009/122906
PCT Pub. Date: Oct. 8, 2009

(65) Prior Publication Data
US 2011/0028942 A1 Feb. 3, 2011

(30) Foreign Application Priority Data
Apr. 1, 2008 (JP) .................................. 2008-095243

(51) Int. Cl.
*A61M 5/178* (2006.01)
(52) U.S. Cl. .................................. 604/167.03; 604/535
(58) Field of Classification Search ............. 604/167.03, 604/167.04, 167.06, 533–536
See application file for complete search history.

(56) References Cited

U.S. PATENT DOCUMENTS

| 5,464,400 A | 11/1995 | Collins |
| 5,591,137 A * | 1/1997 | Stevens .......................... 604/296 |

FOREIGN PATENT DOCUMENTS

| GB | 2 331 339 | 5/1999 |
| JP | 7-198083 | 8/1995 |
| JP | 2004-129741 | * 4/2004 |

OTHER PUBLICATIONS

International Search Report issued Jun. 9, 2009 in International (PCT) Application No. PCT/JP2009/055229.

* cited by examiner

*Primary Examiner* — Kevin C Sirmons
*Assistant Examiner* — Emily Schmidt
(74) *Attorney, Agent, or Firm* — Wenderoth, Lind & Ponack, L.L.P.

(57) ABSTRACT

Body pressing surfaces of A and B members at which a body of the packing is to be pressed come into contact with the body of the packing, and the body starts to be pressed. Then, projections of the packing are pressed with a delay from the pressing of the body because of gaps provided between the projections of the packing and projection-pressing surfaces at which the projections of the packing are to be pressed.

6 Claims, 13 Drawing Sheets

CATHETER CONNECTOR

TECHNICAL FIELD

The present invention relates to connectors intended for, for example, indwelling catheters for epidural anesthesia.

BACKGROUND ART

A catheter connector disclosed in Patent Document 1 below is separable into an A (first) member and a B (second) member that include a through hole into which a catheter is to be inserted, a drug-solution injection section communicating with the through hole, and threads engaging with each other. A catheter insertion port of the through hole and the drug-solution injection section are provided in different ones, respectively, of the A and B members. A packing having a through hole into which the catheter is to be inserted is mounted on either of the A and B members. After insertion of a catheter from the catheter insertion port of the through hole into the through hole of the packing, the A and B members are caused to threadably engage each other such that the packing is compressed with the A and B members, whereby the catheter is fixed. A syringe or the like is connected to the drug-solution injection section, and a drug solution is fed into the catheter.

The packing is a cylindrical body having cylindrical projections projecting from the centers of both end faces, respectively, thereof, the projections each having a smaller diameter than the body. Thus, when the packing is compressed, the through hole is contracted, whereby the pressure with which the catheter is fastened is evened out over the entire length of the packing. Consequently, the catheter is prevented from being squashed easily, whereas the catheter is assuredly fixed. Conventionally, when the packing is compressed, the body and the projections are compressed simultaneously.

[Patent Document 1] Japanese Unexamined Patent Application Publication No. 2004-129741

SUMMARY OF THE INVENTION

It is an object of the present invention to further even out, over the entire length of the packing, the pressure with which the catheter is fastened when the packing is compressed and the through hole is contracted, and to thus further prevent the catheter from being squashed easily while assuredly fixing the catheter.

The present invention provides a catheter connector that is separable into an A (first) member and a B (second) member that include a through hole into which a catheter is to be inserted, a drug-solution injection section communicating with the through hole, and threads engaging each other. A catheter insertion port of the through hole and the drug-solution injection section are provided in different ones, respectively, of the A and B members. A packing having a through hole into which the catheter is to be inserted is mounted on either of the A and B members. After insertion of a catheter from the catheter insertion port of the through hole into the through hole of the packing, the A and B members are caused to threadably engage each other such that the packing is compressed with the A and B members, whereby the catheter is fixed. A syringe or the like is connected to the drug-solution injection section. A drug solution is fed into the catheter. In the catheter connector, the packing is a cylindrical body having cylindrical projections projecting from the centers of both end faces, respectively, thereof, the projections each having a smaller diameter than the body. In compressing the packing with the A and B members, when body-pressing surfaces of the A and B members at which the body of the packing is to be pressed come into contact with the body of the packing and the body of the packing starts to be pressed, the projections of the packing are pressed with a delay from the pressing of the body because of gaps provided between the projections of the packing and projection-pressing surfaces at which the projections of the packing are to be pressed.

When the body-pressing surfaces of the A and B members at which the body of the packing is to be pressed come into contact with the body of the packing and the body starts to be pressed, the projections of the packing are pressed with a delay from the pressing of the body by providing the gaps between the projections of the packing and the projection-pressing surfaces at which the projections of the packing are to be pressed. Thus, compared with the case where the body and the projections are pressed simultaneously, the pressure (contact pressure) with which the catheter is fastened is further evened out over the entire length of the packing.

Figure 9:
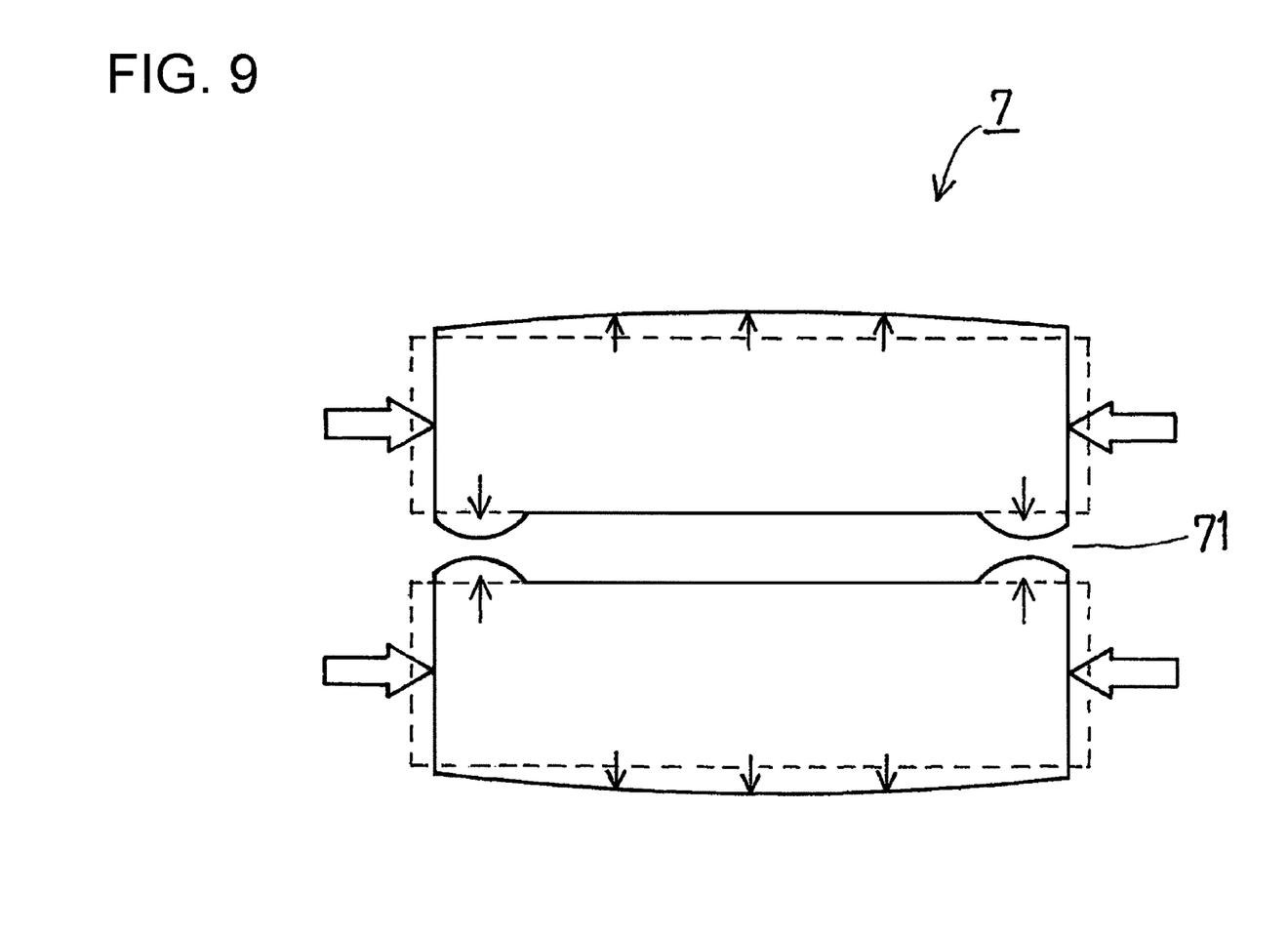
FIG. 9 is an illustrative diagram showing a compressed state of a packing according to a comparative example.

FIG. 9 schematically shows the deformation of a (projection-less) cylindrical packing 7 occurring when the packing 7 is pressed. The shape before compression is shown by dashed lines, and the shape after compression is shown by solid lines. When compressive forces are applied from both sides of the packing, the outer circumferential region tends to deform outward, the inner circumferential region tends to deform locally at both ends, and the central region tends to undergo substantially no deformation.

Figure 11:
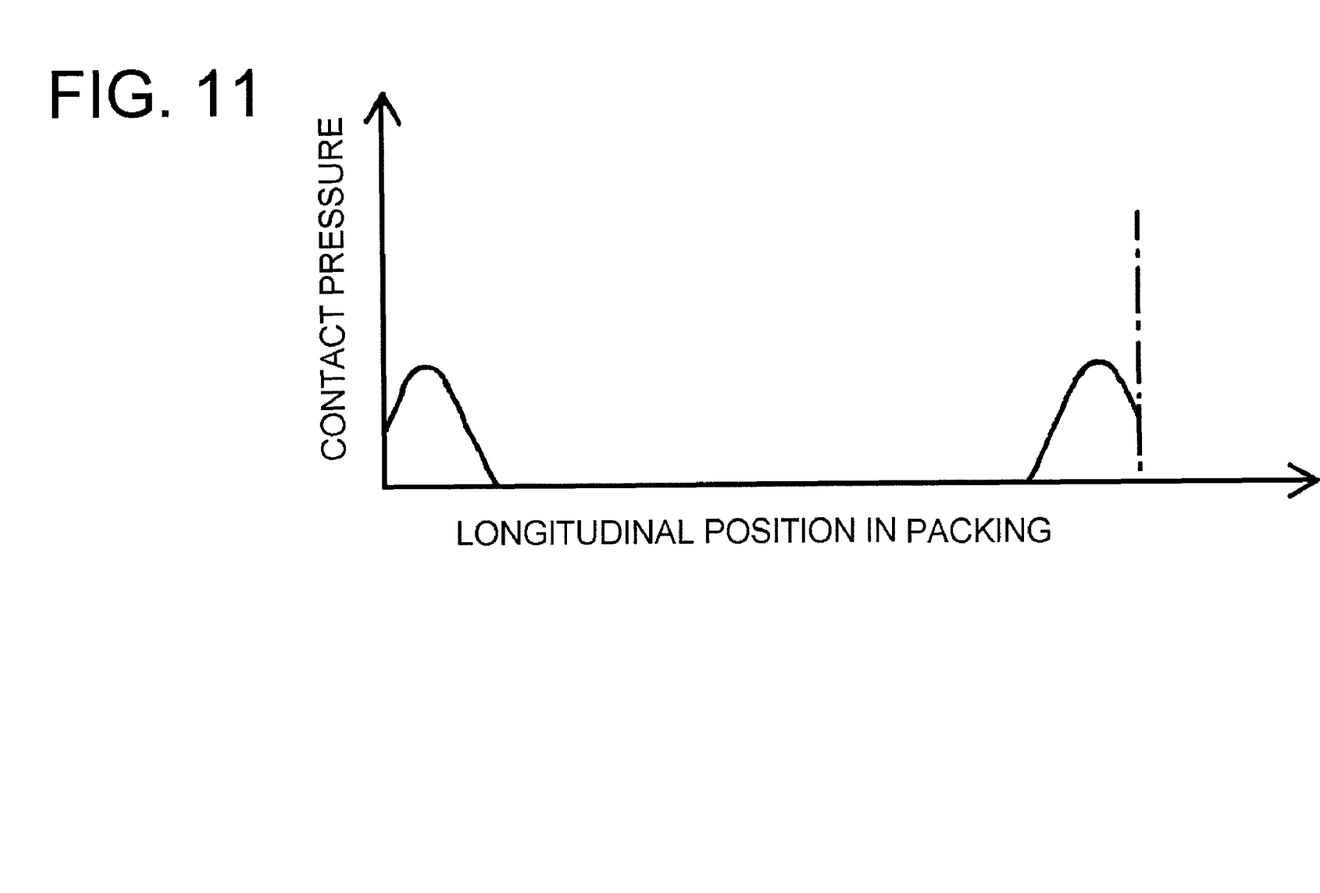
FIG. 11 is an illustrative diagram showing the distribution of contact pressure in the packing according to the comparative example.

FIG. 11 shows the distribution of contact pressure when the cylindrical packing 7 is pressed. The contact pressure occurs locally only at both longitudinal ends of the packing.

Figure 10:
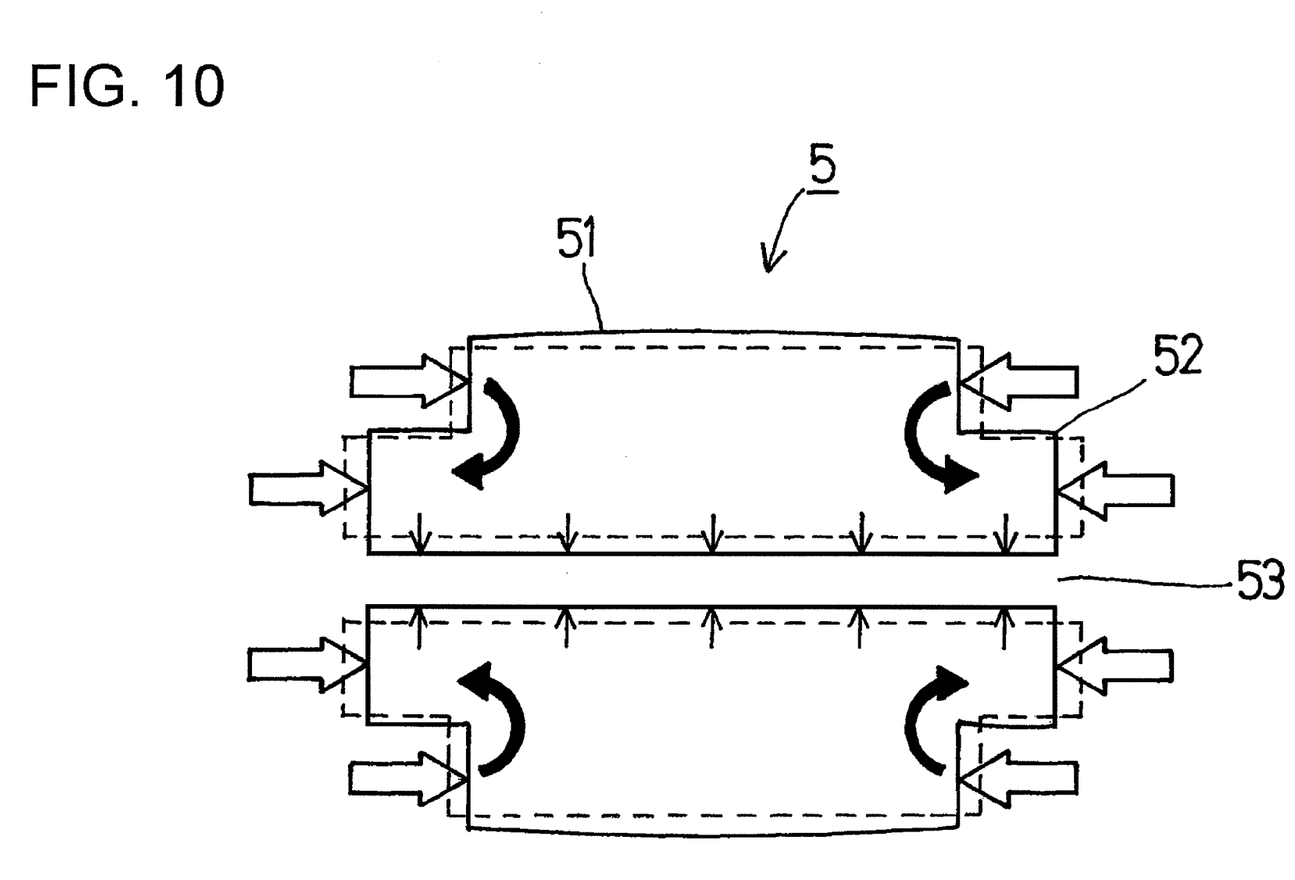
FIG. 10 is an illustrative diagram showing a compressed state of a packing according to an embodiment.

FIG. 10 schematically shows the deformation of a packing that is a cylindrical body having projections on both end faces thereof. The shape before compression is shown by dashed lines, and the shape after compression is shown by solid lines. When compressive forces are applied to both sides of the body of the packing, the packing material tends to deform inward at the ends of the body. However, because of the existence of the projections, the direction of deformation is changed toward the projections (bold black arrows), whereby the tendency that the outer circumferential region deforms outward is suppressed, whereas the inner circumferential region tends to deform inward.

That is, by providing projections on both end faces of the packing, the local deformation occurring at the ends of the inner circumferential region of the body (if the projections are not provided) is dispersed. At the same time, the tendency that the outer circumferential region of the body deforms outward is suppressed, whereas the inner circumferential region of the body tends to deform inward. Consequently, the contact pressure with which the catheter is fastened is evened out.

If the projections of the packing are pressed with a delay from the pressing of the body, the tendency of redirection (the bold black arrows) of the inward deformation at the ends of the body toward the projections is enhanced, whereby the contact pressure is further evened out over the entire length of the packing.

Figure 12:
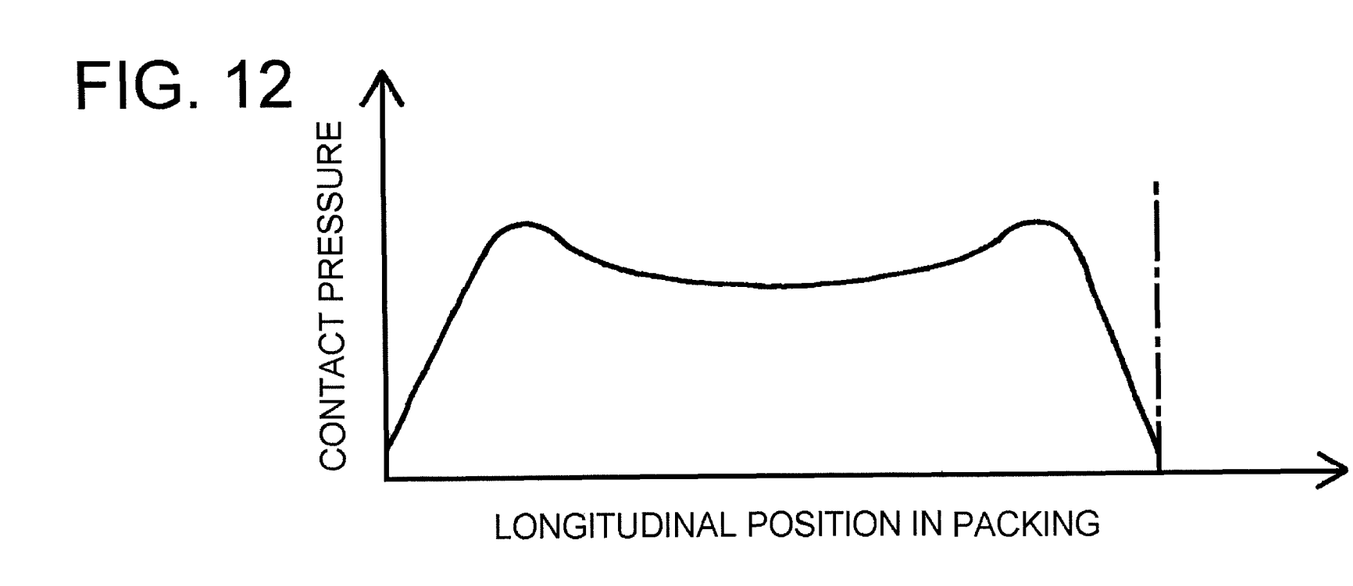
FIG. 12 is an illustrative diagram showing the distribution of contact pressure in a packing according to a comparative example.
Figure 13:
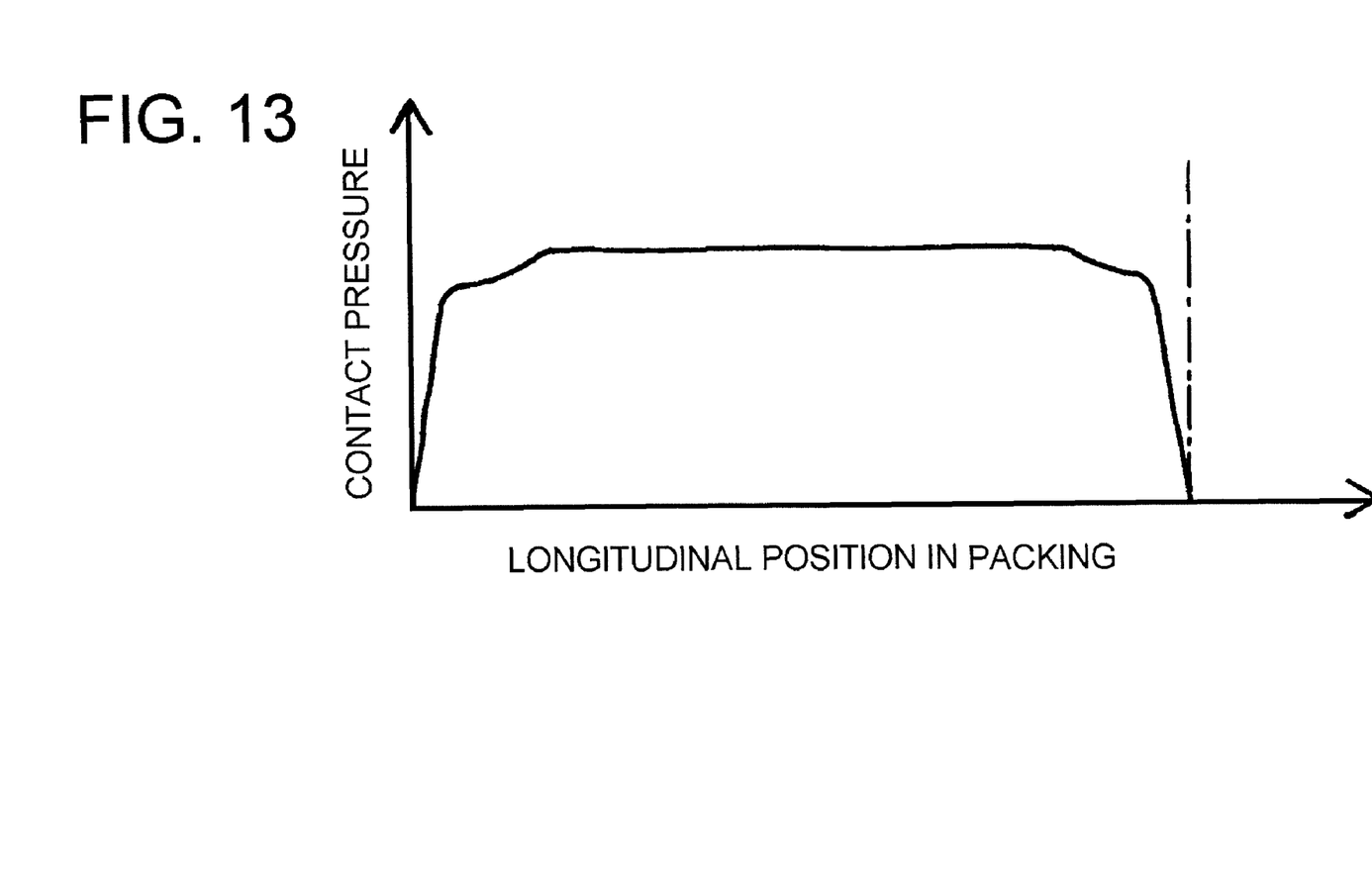
FIG. 13 is an illustrative diagram showing the distribution of contact pressure in the packing according to the embodiment.

FIG. 12 shows the distribution of contact pressure in a case where a packing that is a cylindrical body having projections at both end faces thereof is pressed at the body and at the projections simultaneously. FIG. 13 shows the distribution of contact pressure in a case where the projections are pressed with a delay from the pressing of the body.

In the case shown in FIG. 12, the contact pressure is locally large at regions near the ends of the body. If the amount of compression of the packing is increased so as to assuredly fix the catheter, the catheter may be squashed at the foregoing regions. In addition, the contact pressure is small in the central region of the body.

In the case shown in FIG. 13, the contact pressure is almost even and there are no regions where the contact pressure is locally large. Therefore, the catheter can be assuredly fixed without the possibility of the catheter being squashed.

The present invention also provides the connector described above, in which the gaps each have a length t of 0.05 to 0.3 mm and are each smaller than or equal to 30% of a final amount of compression of the body.

At the moment the body-pressing surfaces at which the body of the packing is to be pressed come into contact with the body and the body starts to be pressed, the length t of each of the gaps between the projections of the packing and the projection-pressing surfaces at which the projections are to be pressed is considered to be adequate at 0.05 to 0.3 mm and is desirably smaller than or equal to 30% of the final amount of contraction of the body.

If the gaps are each smaller than 0.05 mm, the packing may not be able to be pressed as intended because of dimensional errors produced in manufacturing processes, and the effect of evening the contact pressure may be insufficient.

If the gaps are each larger than 0.3 mm, or larger than 30% of the final amount of compression of the body, the gaps may be too large and the contact pressures acting on the projections may be extremely small.

The present invention also provides the connector described above, in which the projections each have a length $L_2$ that is 15 to 25% of a length $L_1$ of the body.

If the projections each have a length smaller than 15% of the length of the body, the redirection of deformation indicated by the bold black arrows in FIG. 10 may be insufficient, reducing the contact pressure acting on the central region of the body and preventing the evening of the contact pressure.

If the projections each have a length larger than 25% of the length of the body, the contact pressures acting on the tips of the projections may be small, preventing the evening of the contact pressure.

The present invention also provides the connector described above, in which the projections each have an outside diameter $D_2$ that is 55 to 65% of an outside diameter $D_1$ of the body.

If the projections each have an outside diameter smaller than 55% of the outside diameter of the body, the redirection of deformation indicated by the bold black arrows in FIG. 10 may be insufficient, reducing the contact pressure acting on the central region of the body and the contact pressures acting on the projections, preventing the evening of the contact pressure.

If the projections each have an outside diameter larger than 65% of the outside diameter of the body, the redirection of deformation indicated by the bold black arrows in FIG. 10 may be insufficient, reducing the contact pressure acting on the central region of the body, preventing the evening of the contact pressure.

In the catheter connector according to the present invention, when the packing is compressed, the through hole is contracted and the pressure with which the catheter is fastened is significantly evened out over the entire length of the packing, whereby the catheter is highly prevented from being squashed easily while the catheter is assuredly fixed.

REFERENCE NUMERALS 1 connector
2 A member
21 insertion opening
22 through hole
23 thread
24 guide
25 projection
26 body-pressing surface
27 projection-pressing surface
3 B member
31 mounting section
32 through hole
33 thread
34 projection
35 drug-solution injection section
36 narrowed portion
37 body-pressing surface
38 projection-pressing surface
39 space
4 cap
5 packing
51 body
52 projection
53 through hole
6 gap
7 packing
71 through hole
8 catheter

DETAILED DESCRIPTION OF THE INVENTION

Embodiment

Figure 1:
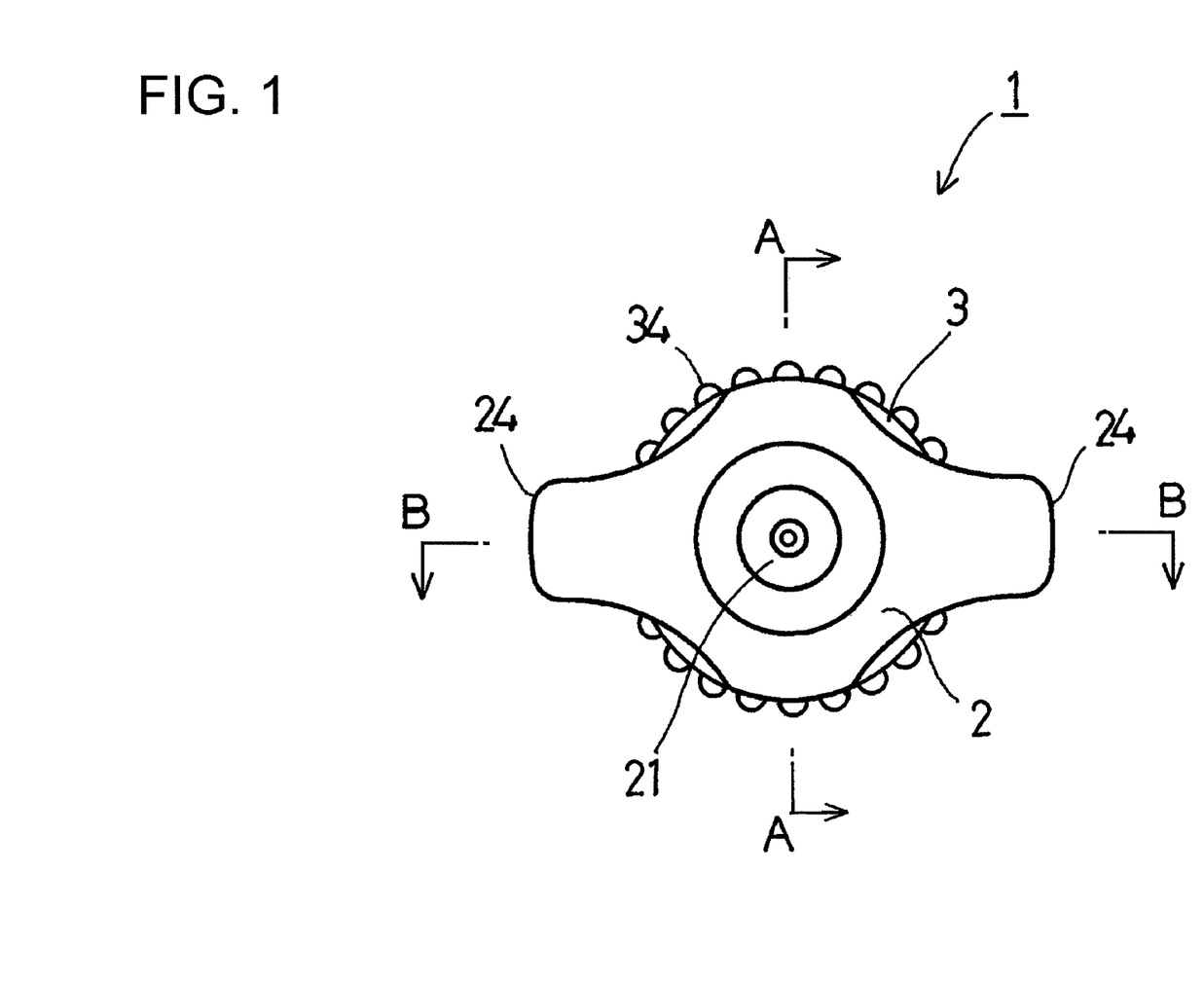
FIG. 1 is a front view of a connector 1.
Figure 2:
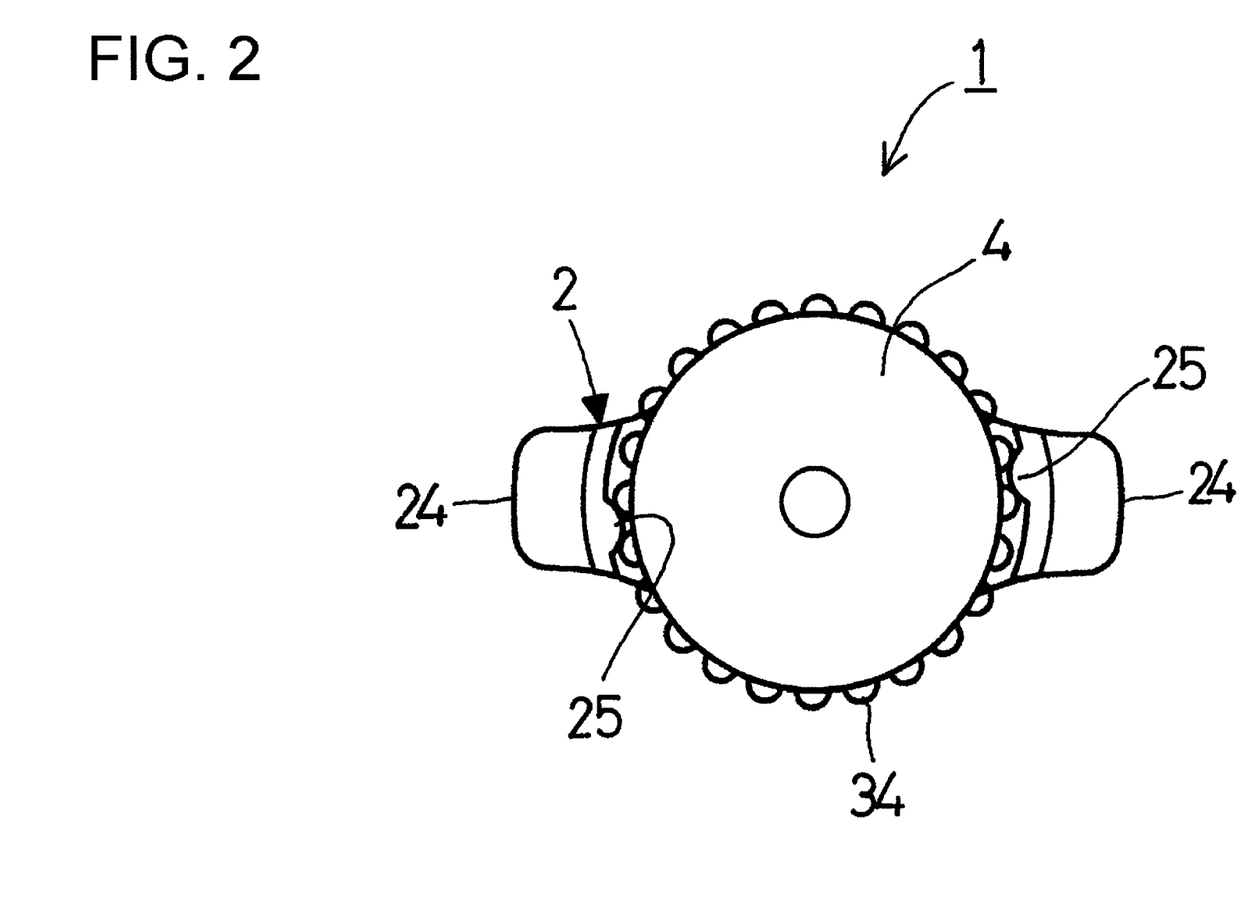
FIG. 2 is a rear view of the connector 1.
Figure 3:
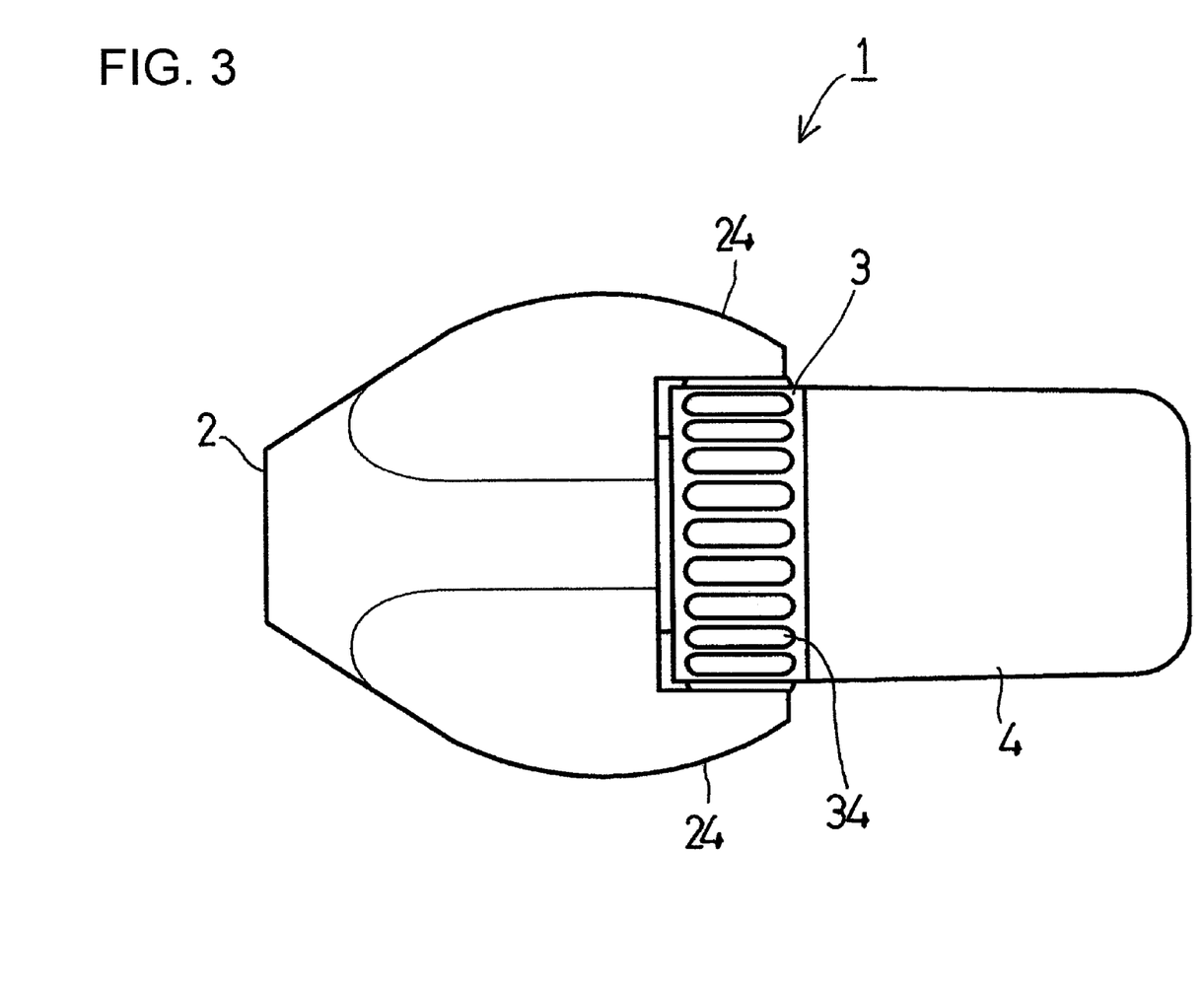
FIG. 3 is a plan view of the connector 1.
Figure 4:
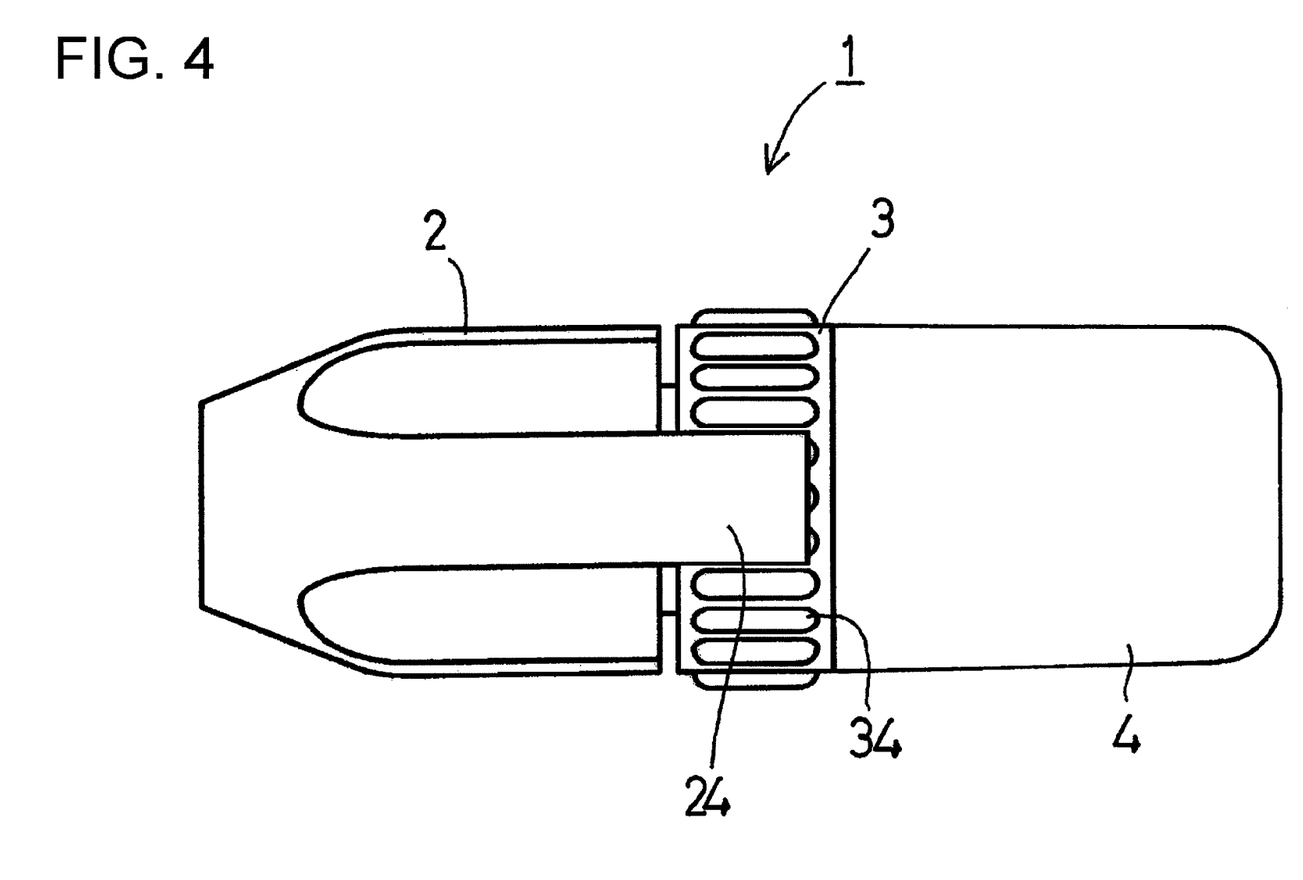
FIG. 4 is a side view of the connector 1.
Figure 5:
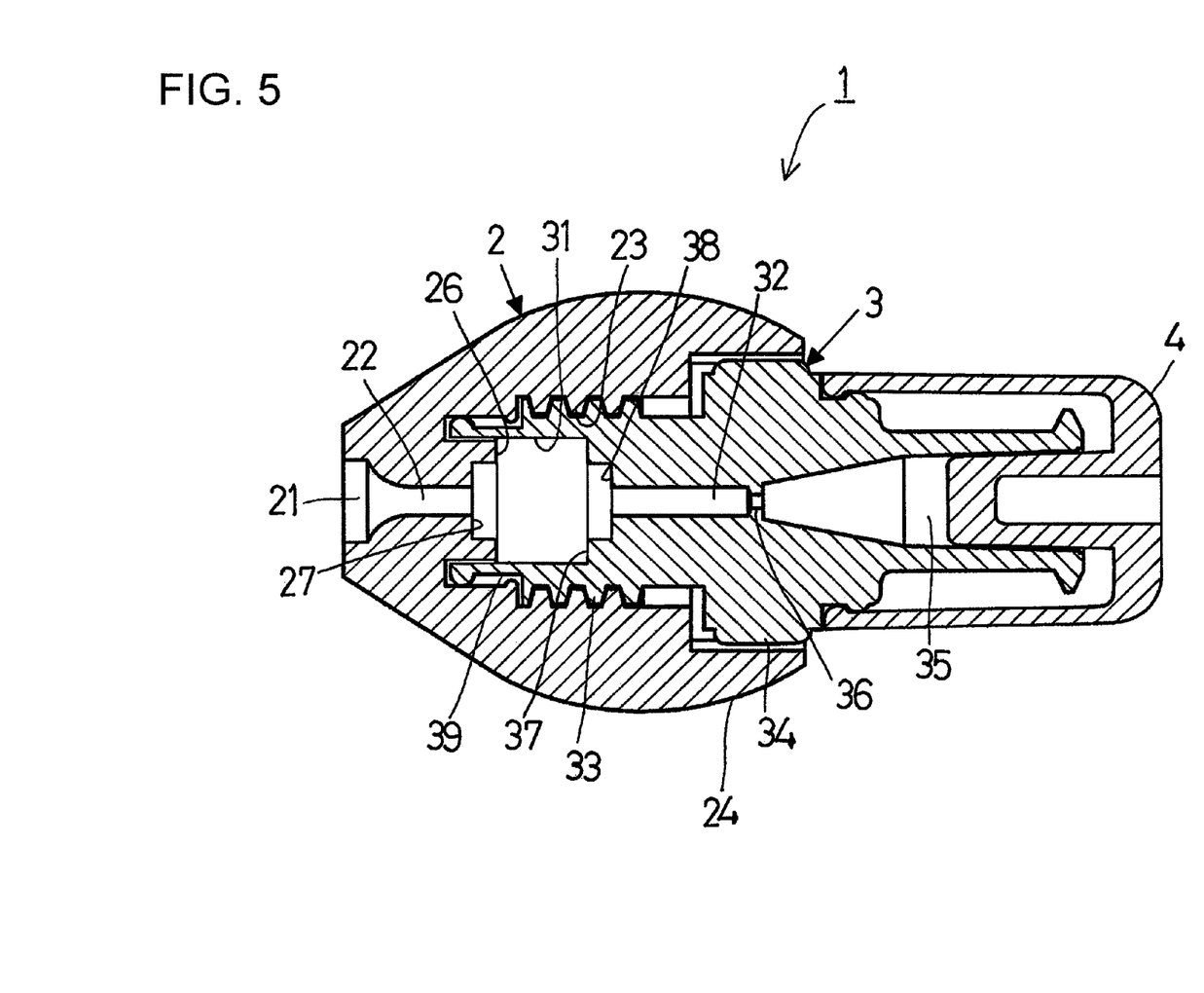
FIG. 5 is a cross-sectional view taken along line B-B in FIG. 1.
Figure 6:
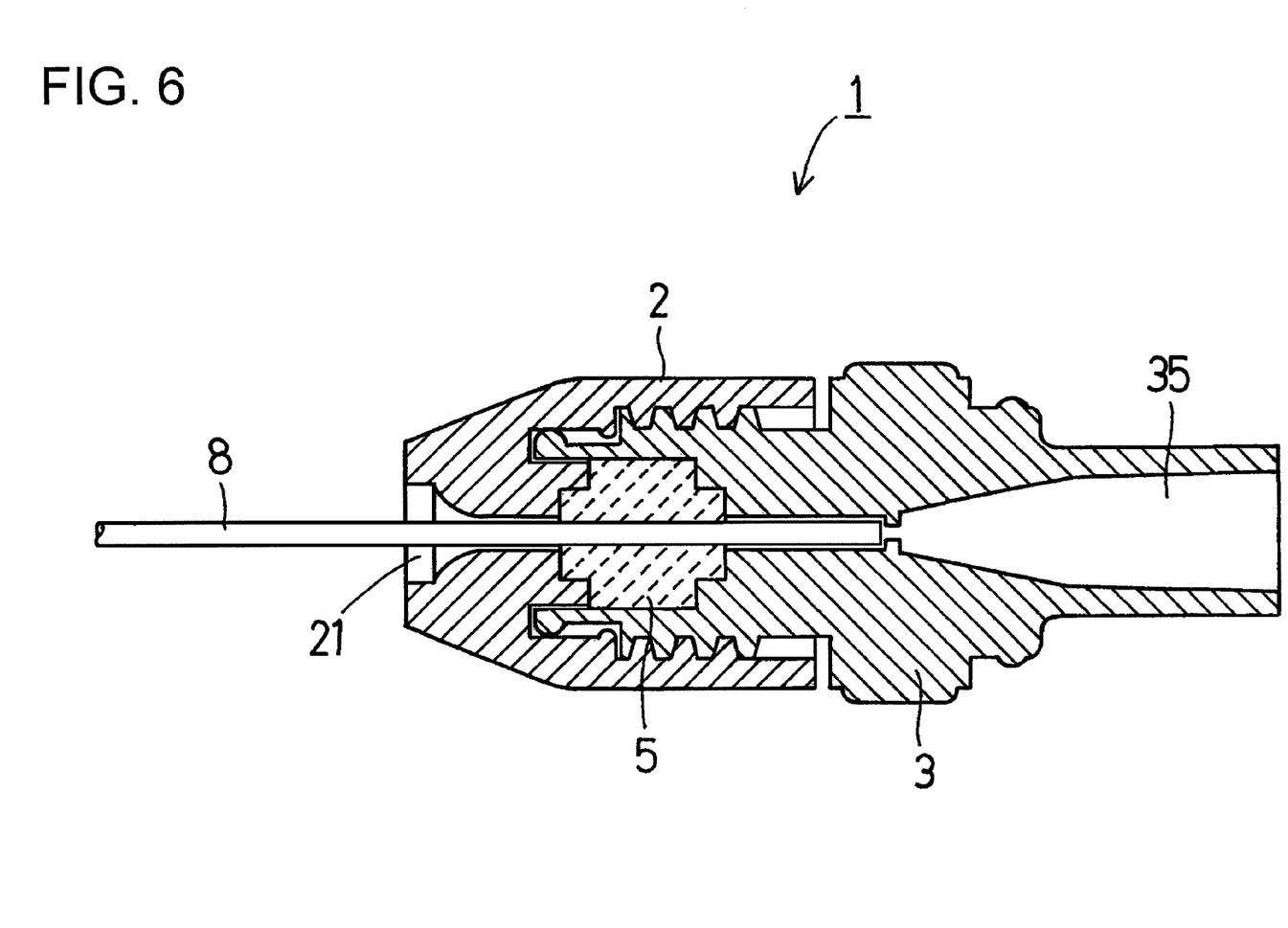
FIG. 6 is an illustrative diagram showing a state of use in a cross section taken along line A-A in FIG. 1.
Figure 7:
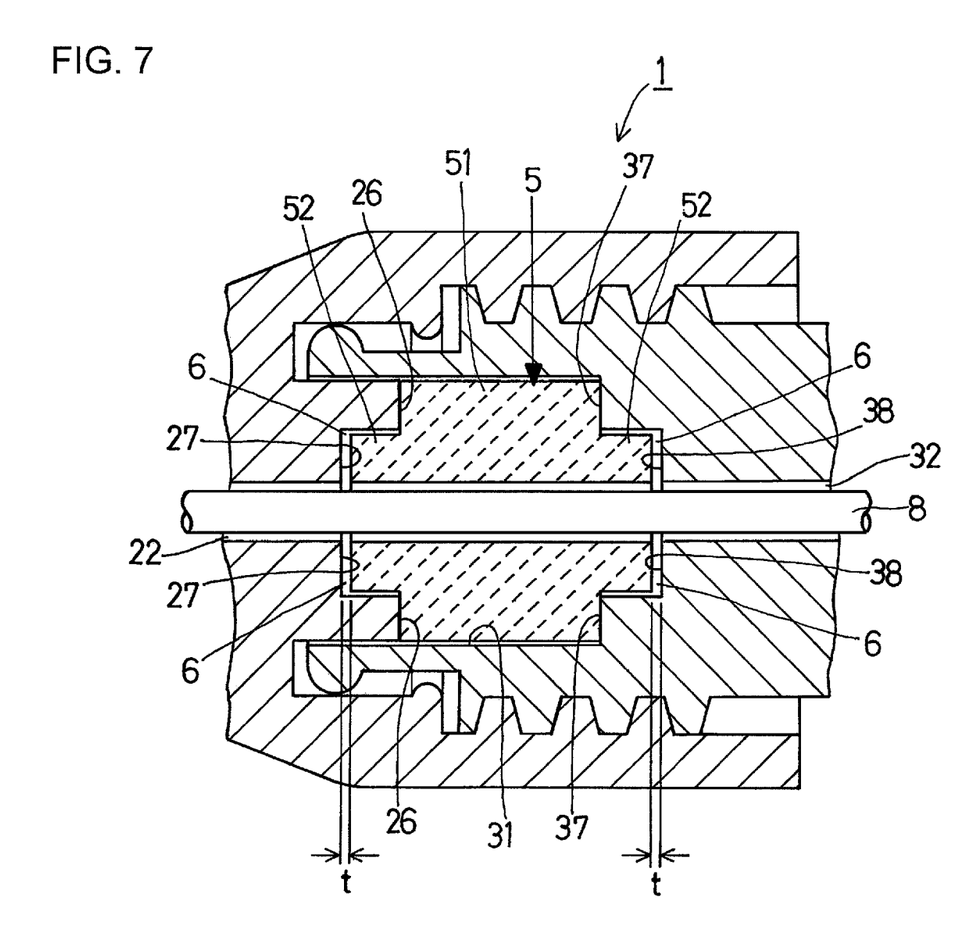
FIG. 7 is an illustrative diagram showing a cross section immediately before a packing 5 is compressed.
Figure 8:
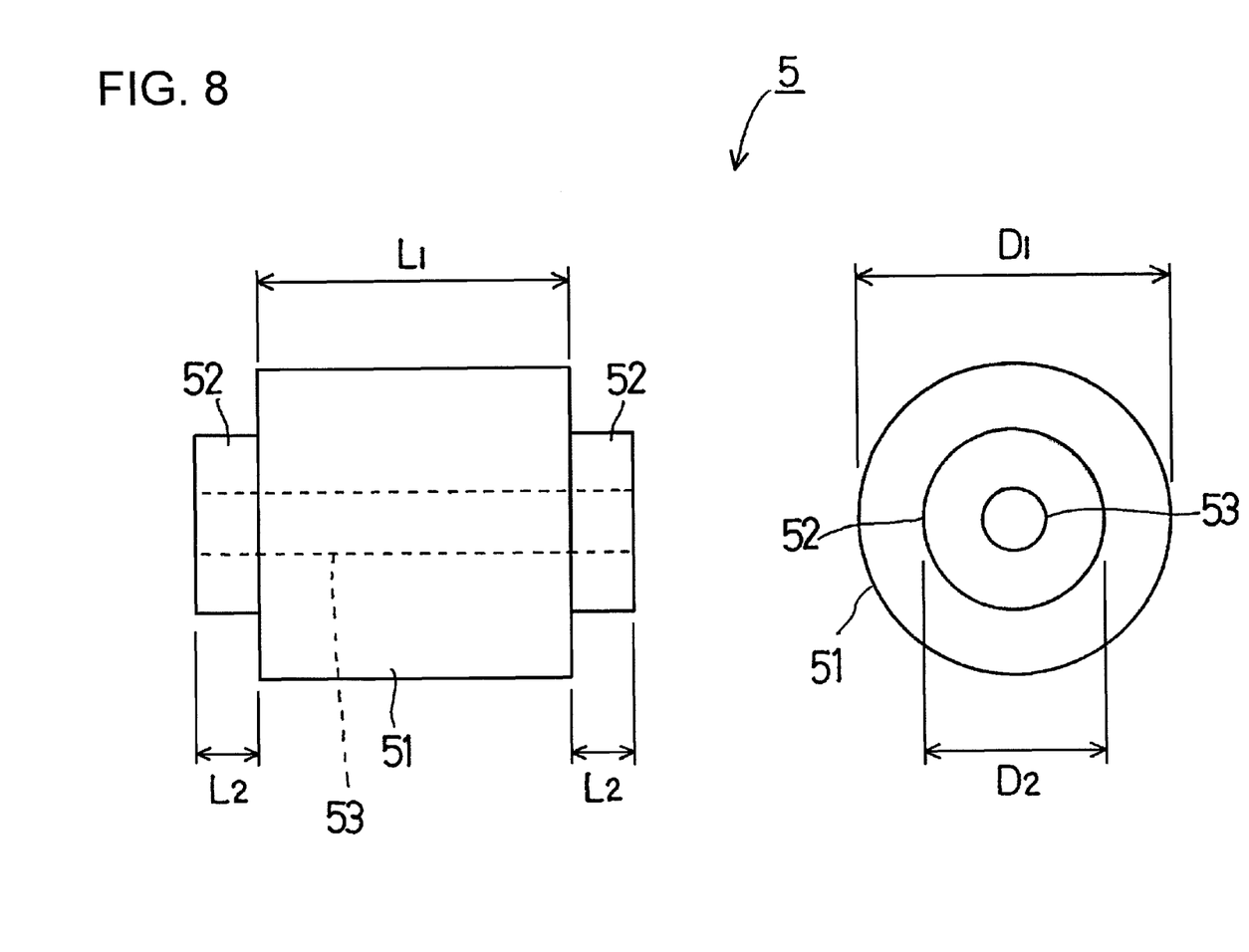
FIG. 8 is an illustrative diagram of the packing 5.

FIGS. 1 to 8 relate to a connector 1 according to an embodiment. FIG. 1 is a front view. FIG. 2 is a rear view. FIG. 3 is a plan view. FIG. 4 is a side view. FIG. 5 is a cross-sectional view taken along line B-B in FIG. 1. FIG. 6 is an illustrative diagram showing a state of use in a cross section taken along line A-A in FIG. 1. FIG. 7 is an illustrative diagram showing a cross section immediately before a packing 5 is compressed. FIG. 8 is an illustrative diagram of the packing 5. In FIG. 5, the packing is omitted. In FIG. 8, a side view of the packing is shown on the left, and a front view is shown on the right.

The connector 1 includes an A (first) member 2 and a B (second) member 3. The A member 2 is made of plastic and has a substantially shell-like shape. The A member 2 has in the center thereof a through hole 22 into which a catheter 8 is to be inserted, and at the rear thereof a space 39 into which the B member 3 is to be fitted and on the inner circumferential surface of which a thread 23 (an internal thread) is provided. The through hole 22 has at an end thereof in the surface at the tip of the A member 2 an insertion opening 21 from which the catheter is to be inserted. The A member 2 also has on the outer circumference thereof two guides 24 extending to the rear over the B member 3. The guides 24 each have on the inner side face thereof a projection 25 received between projections 34 provided on the B member.

The B member 3 is made of plastic and has a substantially cylindrical shape. The B member 3 has at the center thereof a through hole 32 into which the catheter 8 is to be inserted, and on the outer circumference at an inner end thereof a thread 33 (an external thread) so as to be screwed into the space 39 of the A member 2. The packing 5 is mounted in a mounting section 31 provided in the form of a hole having a substantially columnar shape inside the inner end. The through hole 32 has a narrowed portion 36. A drug-solution injection section 35 is provided on the rear side of the narrowed portion 36. The drug-solution injection section 35 is stopped with a detachable cap 4, which is removed (FIG. 6) when used. The B member 3 has on the outer circumferential surface thereof a number of projections 34 arranged in the circumferential direction. When the A and B members are rotated relative to each other, the A and B members rotate with the projections 25 of the A member received between the projections 34 of the B member, thereby rotating by units of a specific angle. As shown in FIG. 6, the B member is connected to the A member by screwing the inner end (the tip) thereof into the space 39 provided in the inner-end (rear-end) face of the A member.

As shown in FIG. 8, the packing 5 made of an elastic material such as rubber includes a cylindrical body 51 and cylindrical projections 52 and 52 projecting concentrically (coaxially) from the centers of both end faces of the body 51 and each having a smaller diameter than the body, with a through hole 53 passing in the center thereof from one of the projections to the other. The body 51 has a length $L_1$ of 5 mm and an outside diameter $D_1$ of 5 mm. The projections 52 and 52 each have a length $L_2$ of 1 mm and an outside diameter $D_2$ of 3 mm, $L_2$ being 20% of $L_1$, $D_2$ being 60% of $D_1$. The inside diameter of the through hole 53 is 1 mm.

In a state where the A member 2 and the B member 3 loosely engage each other (a state where the packing 5 is not compressed), the catheter 8 is inserted from the insertion opening 21 at the tip of the A member into the through hole 22, then the through hole 53 of the packing 5, and then the through hole 32 of the B member. The distal tip of the catheter cannot advance any farther after reaching the narrowed portion 36. Subsequently, when the B member is rotated relative to the A member, as shown now in FIG. 7, body-pressing surfaces 26 and 37 of the A and B members come into contact with both end faces of the packing body 51. This is the state immediately before the body starts to be compressed. In this state, gaps 6 (each having a length t) are provided between projection-pressing surfaces 27 and 38 of the A and B members and the end faces of the packing projections 52. When the B member is rotated relative to the A member, the packing body 51 is first compressed, the packing projections are then compressed, and the through hole 53 is then contracted, whereby the catheter is fixed. In the embodiment, t is defined to be 0.1 mm, and the final amount of compression of the body 51 is defined to be 0.68 mm. That is, t is about 15% of the final amount of compression of the body.

FIG. 12 shows the distribution of contact pressure in a case where a packing the same as that of the embodiment is pressed at the body and at the projections simultaneously (a state where t=0). In this case, two peaks occur near the ends of the body, and the contact pressure in the central region is about 60% of the peaks.

FIG. 13 shows the distribution of contact pressure in the connector 1 according to the embodiment. By pressing the packing projections with a delay from the pressing of the body, the pressure with which the catheter is fastened is substantially evened out over the entire length of the packing. Thus, according to the present invention, the evenness in contact pressure is improved significantly.

The invention claimed is:

1. A catheter connector comprising:
a first member and a second member separable from each other, a through-hole extending through said first member and said second member for receiving a catheter to be inserted therein, said first member and second member including:
a drug-solution injection section communicating with said through hole;
threads configured to allow engagement between said first member and said second member; and
a catheter insertion port communicating with said through hole, each of said drug-solution injection section and said catheter insertion port being provided in a respective different one of said first member and said second member; and
a packing having a through hole into which the catheter is to be inserted, said packing being mounted on one of said first member and said second member so that threadable engagement of said first member and said second member causes compression of said packing and fixing of the catheter when the catheter extends through the through hole of the packing, whereby a syringe is connectable to said drug-solution injection section to feed a drug solution into the catheter;
wherein said packing has a cylindrical body and cylindrical projections each projecting from a center of a respective axial end face of said body, said projections each having a smaller diameter than said body;
wherein said first member, said second member, and said packing are configured and arranged so that, when said packing is compressed via said first member and said second member, body-pressing surfaces of said first member and said second member for pressing said body of said packing contact and press said body of said packing, and pressing of said projections of said packing is delayed from the pressing of said body due to gaps formed between said projections of said packing and projection-pressing surfaces at which said projections of said packing are to be pressed; and
wherein the gaps each have a length t of 0.05 to 0.3 mm and are each smaller than or equal to 30% of a final amount of compression of the body.

2. The connector according to claim 1, wherein the projections each have a length that is 15 to 25% of a length of the body.

3. The connector according to claim 1, wherein the projections each have an outside diameter that is 55 to 65% of an outside diameter of the body.

4. A catheter connector comprising:
a first member and a second member separable from each other, a through-hole extending through said first member and said second member for receiving a catheter to be inserted therein, said first member and second member including:
- a drug-solution injection section communicating with said through hole;
- threads configured to allow engagement between said first member and said second member; and
- a catheter insertion port communicating with said through hole, each of said drug-solution injection section and said catheter insertion port being provided in a respective different one of said first member and said second member; and a packing having a through hole into which the catheter is to be inserted, said packing being mounted on one of said first member and said second member so that threadable engagement of said first member and said second member causes compression of said packing and fixing of the catheter when the catheter extends through the through hole of the packing, whereby a syringe is connectable to said drug-solution injection section to feed a drug solution into the catheter;

wherein said packing has a cylindrical body and cylindrical projections each projecting from a center of a respective axial end face of said body, said projections each having a smaller diameter than said body;

wherein said first member, said second member, and said packing are configured and arranged so that, when said packing is compressed via said first member and said second member, body-pressing surfaces of said first member and said second member for pressing said body of said packing contact and press said body of said packing, and pressing of said projections of said packing is delayed from the pressing of said body due to gaps formed between said projections of said packing and projection-pressing surfaces at which said projections of said packing are to be pressed; and wherein the projections each have a length that is 15 to 25% of a length of the body.

5. The connector according to claim 4, wherein the projections each have an outside diameter that is 55 to 65% of an outside diameter of the body.

6. A catheter connector comprising:
a first member and a second member separable from each other, a through-hole extending through said first member and said second member for receiving a catheter to be inserted therein, said first member and second member including:
- a drug-solution injection section communicating with said through hole;
threads configured to allow engagement between said first member and said second member; and
- a catheter insertion port communicating with said through hole, each of said drug-solution injection section and said catheter insertion port being provided in a respective different one of said first member and said second member; and a packing having a through hole into which the catheter is to be inserted, said packing being mounted on one of said first member and said second member so that threadable engagement of said first member and said second member causes compression of said packing and fixing of the catheter when the catheter extends through the through hole of the packing, whereby a syringe is connectable to said drug-solution injection section to feed a drug solution into the catheter;

wherein said packing has a cylindrical body and cylindrical projections each projecting from a center of a respective axial end face of said body, said projections each having a smaller diameter than said body;

wherein said first member, said second member, and said packing are configured and arranged so that, when said packing is compressed via said first member and said second member, body-pressing surfaces of said first member and said second member for pressing said body of said packing contact and press said body of said packing, and pressing of said projections of said packing is delayed from the pressing of said body due to gaps formed between said projections of said packing and projection-pressing surfaces at which said projections of said packing are to be pressed; and wherein the projections each have an outside diameter that is 55 to 65% of an outside diameter of the body.

* * * * *